(12) United States Patent
Fertig et al.

(10) Patent No.: US 7,208,491 B2
(45) Date of Patent: Apr. 24, 2007

(54) N-MONOACYLATED O-PHENYLENEDIAMINES

(75) Inventors: Georg Fertig, Penzberg (DE); Frank Herting, Penzberg (DE); Manfred Kubbies, Penzberg (DE); Anja Limberg, Munich (DE); Ulrike Reiff, Penzberg (DE); Michael Weidner, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 409 days.

(21) Appl. No.: 10/771,188

(22) Filed: Feb. 3, 2004

(65) Prior Publication Data

US 2004/0157841 A1 Aug. 12, 2004

(30) Foreign Application Priority Data

Feb. 7, 2003 (EP) .................. 03002820

(51) Int. Cl.
C07D 333/56 (2006.01)
A61K 31/5377 (2006.01)
A61K 31/454 (2006.01)
A61K 31/4439 (2006.01)

(52) U.S. Cl. ............... 514/232.2; 514/320; 514/337; 514/419; 514/422; 544/143; 544/145; 546/201; 546/202; 546/278.1; 546/281.1; 548/494; 548/525; 549/57

(58) Field of Classification Search ............... 514/320, 514/422, 337, 419, 443, 469; 544/145; 546/202; 548/494; 549/57
See application file for complete search history.

(56) References Cited

U.S. PATENT DOCUMENTS

| 3,810,910 A | 5/1974 | Meyer et al. |
| 5,137,918 A | 8/1992 | Weiershausen et al. |
| 5,395,849 A | 3/1995 | Wittman et al. |
| 6,869,953 B2* | 3/2005 | Haag et al. ............ 514/247 |

FOREIGN PATENT DOCUMENTS

| DE | 2 062 265 | 5/1972 |
| EP | 242 851 | 10/1987 |
| EP | 847 992 | 6/1998 |
| EP | 974 576 | 1/2000 |
| FR | 2 167 954 | 8/1973 |
| GB | 2 165 537 | 4/1986 |
| JP | 11 269140 | 10/1999 |
| JP | 11 269146 | 10/1999 |
| WO | WO 01/38322 | 5/2001 |
| WO | WO 01/70675 | 9/2001 |
| WO | WO 02/30894 A2 | 4/2002 |
| WO | WO 02/070468 A2 | 9/2002 |
| WO | WO 03/011851 | 2/2003 |
| WO | WO 03/013484 | 2/2003 |

OTHER PUBLICATIONS

Koyama et al., Blood, 96, pp. 1490-1495 (2000).
Rastogi et al., Indian J. Chem., Sect.B, 21B, pp. 485-487 (1982).
Moll et al., Z. Chem., 17, pp. 132-134 (1977).
Hassan et al., Indian J. Chem., 39B, pp. 764-768 (2000).
Moody et al., J. Chem. Soc. Perkin Trans., 1, pp. 1333-1337 (1984).
Julia et al., Bull. Soc. Chem. Fr., 6, pp. 2046-2057 (1973).
Misra et al., Spectrochim. Acta Part A 57, pp. 2795-2808 (2001).
Reichenstein et al., Helv. Chim. Acta, 18, pp. 816-826 (1935).
Beilstein Institute for Organic Chemistry, XP002297054, Database accession No. 4529791, Abstract, & Prewysz-Kwinto: Chem. Heterocycl. Compd., vol. 23, No. 6 pp. 624-627 (1987).

* cited by examiner

*Primary Examiner*—Kamal A. Saeed
(74) *Attorney, Agent, or Firm*—George W. Johnston; Patricia S. Rocha-Tramaloni; Brian C. Remy

(57) ABSTRACT

Mono-acylated o-phenylendiamines derivatives of formula I

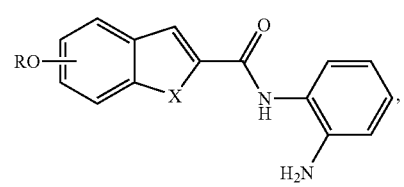

wherein X and R are as described herein, have been found useful for the treatment of diseases mediated by the inhibition of histone deacetylase, such as cancer.

18 Claims, No Drawings

N-MONOACYLATED O-PHENYLENEDIAMINES

BACKGROUND OF THE INVENTION

The present invention generally relates to novel antitumor agents and pharmaceutically acceptable acceptable salts thereof, processes for the manufacture of these novel compounds and medicaments, containing them. The compounds of the invention have antiproliferative and differentiation-inducing activity, which results in inhibition of tumor cell proliferation, induction of apoptosis and inhibition of invasion. The invention concerns thus also the use of such compounds for the treatment of diseases such as cancer and for the manufacture of corresponding medicaments.

Cancer is one of the major causes of death. Cancer exceeds heart and cerebrovascular diseases in causing death. Accordingly, many studies have been conducted with enormous expense and time to overcome cancer. However, despite a variety of therapies such as surgical operation, radiation therapy and chemotherapy, there is still a great need for improved anticancer therapeutics. Among these therapies, chemotherapy is one of the main areas for cancer treatment. Most drugs show their effect by inhibiting DNA from expressing their cytotoxicity and as a result, injuring tumor cells. However, chemotherapy lacks selectivity and consequently, does not sufficiently differentiate between tumor cells and normal cells, and therefore, adverse reactions expressed in normal cells have limited their use in therapy. Up to now, no satisfactory drugs are believed to have been discovered, and thus, an anticancer drug with reduced toxicity, better tolerability and a high therapeutic effect is very much desired.

Transcriptional regulation is a major event in cell differentiation, proliferation, and apoptosis. Transcriptional activation of a set of genes determines cell destination and for this reason transcription is tightly regulated by a variety of factors. One of its regulatory mechanisms involved in the process is an alteration in the tertiary structure of DNA, which affects transcription by modulating the accessibility of transcription factors to their target DNA segments. Nucleosomal integrity is regulated by the acetylation status of the core histones. In a hypoacetylated state, nucleosomes are tightly compacted and thus are nonpermissive for transcription. On the other hand, nucleosomes are relaxed by acetylation of the core histones, with the result being permissiveness to transcription. The acetylation status of the histones is governed by the balance of the activities of histone acetyl transferase (HAT) and histone deacetylase (HDAC). Recently, HDAC inhibitors have been found to arrest growth and induce apoptosis in several types of cancer cells, including colon cancer cells, T-cell lymphoma cells, and erythroleukemic cells. Given that apoptosis is a crucial factor for cancer progression, HDAC inhibitors are promising reagents for cancer therapy as effective inducers of apoptosis (Koyama, Y., et al., Blood 96 (2000) 1490–1495).

EP-A 0 847 992 describes monoacylated o-phenylendiamine derivatives as cell differentiation inducers. The same type of compounds is also the subject of EP-A 0 242 851. The compounds described in these applications are almost exclusively o-phenylene derivatives monoacylated with derivatives of benzoic acid.

Monoacylated o-phenylendiamines are known in the art as precursors for the preparation of the corresponding benzimidazoles, such preparation methods are e.g. described in DE-A 2 062 265; FR 2 167 954; Rastogi, R., and Sharma, S., Indian J. Chem., Sect. B, 21B (5) (1982) 485–487; Moll, R., et al., Z. Chem. 17 (1977) 133–134; and Hassan H., et al., Indian J. Chem. 39B (2000) 764–768.

As can be seen, there exists a need to provide compounds with improved properties such as increased tolerability, less toxicity and less side effects.

SUMMARY OF THE INVENTION

Broadly, the present invention provides compounds of the general formula I

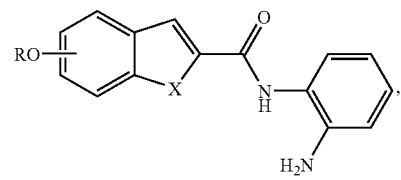

wherein X and R are as hereinbelow described.

The present invention also encompasses pharmaceutically acceptable salts or prodrugs of the compounds of formula I as well as the use of these compounds to produce medicaments.

It has been found that the compounds of the present invention are HDAC inhibitors which have anti-proliferative and differentiation-inducing activity, which results in inhibition of tumor cell proliferation, induction of apoptosis and inhibition of invasion. These compounds are therefore useful for the treatment of diseases such as cancer in humans or animals. Examples of tumors which may be treated, but are not limited to, colon cancers, breast carcinoma (including advanced breast cancer), lung cancer (e.g. adenocarcinoma and including non-small cell lung cancer), prostate cancer including advanced disease, pancreatic cancers, hematopoetic tumors of lymphoid lineage (e.g. acute lymphatic leukemia, B-cell lymphoma, Burkitt's lymphoma), myeloid leukemias (for example, acute myelogenous leukemia (AML)), thyroid follicular cancer, myelodysplastic syndrome (MSD), tumors of mesenchymal origin, melanomas, teratocarcinomas, neuroblastomas, gliomas, benign tumors of the skin (e.g. keratoacanthomas), kidney carcinoma, ovary carcinoma, bladder carcinoma and epidermal carcinoma.

The compounds of the present invention surprisingly show low toxicity, together with a potent anti-proliferative and cell differentiation activity characterized by enhanced acetylation due to inhibition of HDAC.

DETAILED DESCRIPTION OF THE INVENTION

The following definitions of the general terms used in the present description apply irrespective of whether the terms in question appear alone or in combination.

The term "$C_1$–$C_6$-alkyl" as used herein denotes a saturated, linear- or branched chain alkyl group containing 1 to 6 carbon-atoms, for example methyl, ethyl, propyl, isopropyl, 1-butyl, 2-butyl, tert-butyl and the like. Preferred "$C_1$–$C_6$-alkyl" groups have 1, 2 or 3 carbon-atoms.

The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethylammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Ansel, H., et. al., In: Pharmaceutical Dosage Forms and Drug Delivery Systems, 6th ed. (1995), pp. 196 and 1456–1457.

The term "substituted," as in a substituted alkyl, means that the substitution can occur at one or more positions, and, unless otherwise indicated, that the substituents at each substitution site are independently selected from the specified options.

The term "therapeutically effective amount" means an amount of at least one compound of formula I, or a pharmaceutically acceptable salt thereof, that significantly inhibits proliferation and/or prevents differentiation of a human tumor cell, including human tumor cell lines.

In particular, the present invention concerns compounds of the general formula I

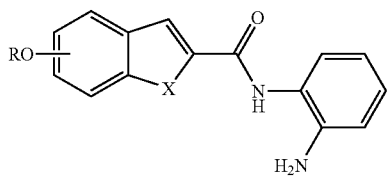

wherein
X represents N, S or O;
R represents $CH_3$—(O—$CH_2CH_2$)n- or $C_1$–$C_6$-alkyl, which alkyl group is monosubstituted with
—$CO_2H$, —OH, $R^1R^2N$—, pyridin-2-yl, pyrrolidin-1-yl, piperidino or morpholino;
$R^1$, $R^2$ independently from each other denote $C_1$–$C_6$ alkyl;
n is 1, 2, 3 or 4;
or a pharmaceutically acceptable salt thereof.

Compounds of the general formula I can contain one or several chiral centers and can then be present in a racemic or in an optically active form. The racemates can be separated according to known methods into the enantiomers. Preferably, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

A preferred embodiment of the invention are compounds of formula I, wherein
X represents N, S or O;
R represents $R^1R^2N$—($C_1$–$C_6$)-alkyl; and
$R^1$, $R^2$ are independently a $C_1$–$C_6$-alkyl group, such as, for example
5-(2-Dimethylamino-ethoxy)-benzo[b]thiophene-2-carboxylic acid (2-amino-phenyl)-amide,
5-(3-Dimethylamino-propoxy)-benzofuran-2-carboxylic acid (2-amino-phenyl)-amide,
7-(3-Dimethylamino-propoxy)-benzofuran-2-carboxylic acid (2-amino-phenyl)-amide,
5-(3-Dimethylamino-propoxy)-benzo[b]thiophene-2-carboxylic acid (2-amino-phenyl)-amide,
7-(2-Dimethylamino-ethoxy)-benzofuran-2-carboxylic acid (2-amino-phenyl)-amide,
7-(2-Diisopropylamino-ethoxy)-benzofuran-2-carboxylic acid (2-amino-phenyl)-amide, or
5-(2-Diisopropylamino-ethoxy)-benzo[b]thiophene-2-carboxylic acid (2-amino-phenyl)-amide.

A further preferred embodiment of the invention are compounds of formula I, wherein
X represents N, S or O;
R represents a group alkyl-(O—$CH_2CH_2$)$_n$—;
n is 1, 2, 3 or 4; such as, for example
5-(2-Methoxy-ethoxy)-1H-indole-2-carboxylic acid (2-amino-phenyl)-amide,
5-(2-Methoxy-ethoxy)-benzo[b]thiophene-2-carboxylic acid (2-amino-phenyl)-amide,
7-(2-Methoxy-ethoxy)-benzofuran-2-carboxylic acid (2-amino-phenyl)-amide,
7-[2-(2-Methoxy-ethoxy)-ethoxy]-benzofuran-2-carboxylic acid (2-amino-phenyl)-amide, or
5-[2-(2-Methoxy-ethoxy)-ethoxy]-benzo[b]thiophene-2-carboxylic acid (2-amino-phenyl)-amide.

A further preferred embodiment of the invention are compounds of formula I, wherein
X represents N, S or O;
R represents $C_1$–$C_6$-alkyl, monosubstituted with pyridin-2-yl, pyrrolidin-1-yl, piperidino, morpholino; such as, for example
7-(Pyridin-2-ylmethoxy)-benzofuran-2-carboxylic acid (2-amino-phenyl)-amide,
5-(Pyridin-2-ylmethoxy)-benzo[b]thiophene-2-carboxylic acid (2-amino-phenyl)-amide,
7-(2-Pyrrolidin-1-yl-ethoxy)-benzofuran-2-carboxylic acid (2-amino-phenyl)-amide,
7-(2-Piperidin-1-yl-ethoxy)-benzofuran-2-carboxylic acid (2-amino-phenyl)-amide, or
5-(2-Morpholin-4-yl-ethoxy)-benzo[b]thiophene-2-carboxylic acid (2-amino-phenyl)-amide.

A further preferred embodiment of the invention are compounds of formula I,
wherein
X represents N, S or O;
R represents $C_1$–$C_6$-alkyl, monosubstituted with —$CO_2H$; such as, for example
2-(2-Amino-phenylcarbamoyl)-benzofuran-7-yloxy]-acetic acid,
2-(2-Amino-phenylcarbamoyl)-benzo[b]thiophene-5-yloxy]-acetic acid, or
2-(2-Amino-phenylcarbamoyl)-1H-indole-5-yloxy]-acetic acid.

A further preferred embodiment of the invention are compounds of formula I,
wherein
X represents N, S or O;
R represents $C_1$–$C_6$-alkyl, monosubstituted with OH; such as, for example
5-(2-Hydroxy-ethoxy)-benzo[b]thiophene-2-carboxylic acid (2-amino-phenyl)-amide,
5-(2-Hydroxy-ethoxy)-1H-indole-2-carboxylic acid (2-amino-phenyl)-amide or
7-(2-Hydroxy-ethoxy)-benzofuran-2-carboxylic acid (2-amino-phenyl)-amide.

Another embodiment of the present invention are compounds of the formula I-A

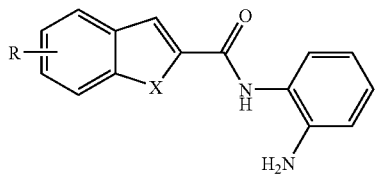

wherein
X and R have the significance given herein before;
and pharmaceutically acceptable salts thereof.

A preferred embodiment of this invention are compounds of formula I-A, wherein
X represents O;
R is $C_1$–$C_6$-alkyl, which alkyl group is monosubstituted with —OH.

Such a compound is, for example,
5-(2-Hydroxy-ethyl)-benzofuran-2-carboxylic acid (2-amino-phenyl)-amide.

A further embodiment of this invention is a process for the manufacture of the o-phenylenediamine derivatives of the general formula I, comprising
a) reacting a compound of formula II

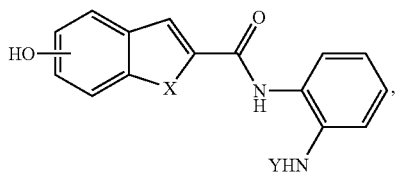

in which
X is as defined above; and
Y represents hydrogen or a suitable amino protecting group with a compound of formula III

R-LG    III, in which
R has the meaning described above; and
   reactive substituents, if present in R, are suitably protected;
LG is a suitable leaving group; and
b) subsequently if Y represents a protected amino group, deprotection of this group as well as cleavage of protecting groups, if present, in R to give a compound of formula I; and
c) conversion, if desired, into its pharmaceutically acceptable salt.

An o-phenylene diamine derivative of the formula I, or a pharmaceutically-acceptable salt thereof, may be prepared by any process known to be applicable to the preparation of chemically-related compounds. Such processes, when used to prepare an o-phenylene diamine derivative of the formula I, or a pharmaceutically-acceptable salt thereof, are provided as a further feature of the invention and are illustrated by the following representative examples in which, unless otherwise stated, X, R, $R^1$ and $R^2$, n have the meanings defined above. Starting materials may be obtained by standard procedures of organic chemistry. The preparation of such starting materials is described within the accompanying examples. Alternatively necessary starting materials are obtainable by analogous procedures to those illustrated which are within the ordinary skill of an organic chemist.

Compounds of formula I are prepared from compounds of the formula II

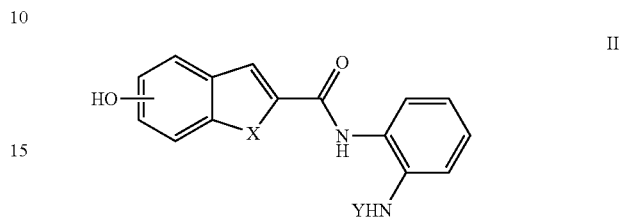

wherein X is as defined above and wherein Y represents hydrogen or a suitable amino protecting group. Protection groups for the amino group are known from peptide chemistry, such protecting groups are for example, benzyloxycarbonyl (cleavage by hydrogenation or hydrobromic acid in acetic acid), t-butoxycarbonyl (cleavage by strong acids, such as, trifluoroacetic acid neat or in dichloromethane, or HCL in dioxane), 9-fluorenmethoxycarbonyl (cleavage by secondary amines, such as, piperidine).

The alcohol of formula II can be converted into an OR-group for example by a substitution reaction with a compound of the general formula III

R-LG    III

Wherein LG is a suitable leaving group for this substitution; examples for LG are Br, Cl, I, tosylate, mesylate.

Wherein R is as defined above and reactive substituents, if present, are suitably protected e.g. a carboxylate substituent is protected for example as the corresponding methyl-, ethyl-, t-butyl-, benzyl or p-methoxybenzyl-ester. A hydroxy substituent is protected for example as the corresponding methyl-, benzyl, tetrahydropyranyl- ethoxyethyl- or silylether.

The reaction is carried out in an inert solvent, for example in methanol, ethanol, acetonitrile, ethyl acetate, dimethylsulfoxide (DMSO), dimethylformamide (DMF) and preferably in the presence of a base, e.g. potassium carbonate ($K_2CO_3$), sodium hydroxide (NaOH), triethylamine, sodium hydride (NaH). If necessary the reaction mixture is heated.

After the alkylation reaction Y and other protecting groups finally have to be cleaved (methods see above) to yield compound I.

The compounds of the formula II can be obtained be cleavage of the $R^3$ group of compounds of the formula IV

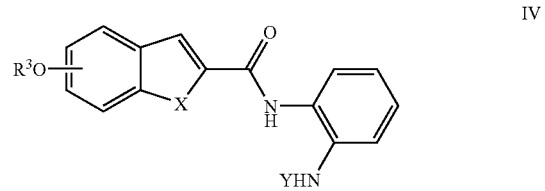

wherein $R^3$ is an alkyl, alkenyl, silyl, optionally substituted benzyl or acyl group. The cleavage of an allyl group can be accomplished for example by a palladium catalyzed reaction in methanol/water in the presence of catalytic amount of p-toluenesulfonic acid.

The cleavage of an benzoyl group can be accomplished by sodium methoxide in methanol.

A preferred method for the preparation of compounds of the formula IV is the reaction of acids of the formula V

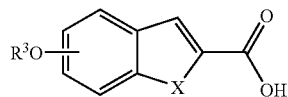

with a compound of the formula VI

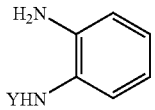

wherein $R^3$, X and Y are as defined above.

This reaction typically involves a two-step one-pot procedure. In the first step, the carboxylate of the formula V is activated by reaction of the compound in an inert solvent or diluent, for example, in dichloromethane, dioxane, or tetrahydrofuran, in the presence of an activating agent.

A suitable reactive derivative of an acid is, for example, an acyl halide, for example an acyl chloride formed by the reaction of the acid and an inorganic acid chloride, for example thionyl chloride or oxalic acid dichloride; a mixed anhydride, for example an anhydride formed by the reaction of the acid and a chloroformate such as isobutyl chloroformate; an active ester, for example an ester formed by the reaction of the acid and a phenol such as pentafluorophenol; an active ester formed by the reaction of the acid and N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as N-3-dimethylaminopropyl-N-ethylcarbodiimid or dicyclohexylcarbodiimide; or the product of the reaction of the acid with N,N'-carbonyldiimidazole; or the product of the reaction of the acid and uroniumsalts such as O-(1H-benzotriazol-1-yl)-N,N,N',N',-tetramethyluronium tetrafluoroborate; or the product of the reaction of the acid and phosphorus based reagents, e.g. bis-(2-oxo-3-oxazolidinyl)-phosphorylchloride. The reaction is carried out between −30° C. and 60° C., conveniently at or below 0° C. In the second step, compound VI is added to the solution to yield compound IV.

These methods are well known to those skilled in the art. In principle, all methods for the synthesis of amides as used in peptide chemistry as described in e.g. Houben-Weyl, Methoden der organischen Chemie, Vols. XV/1 and XV/2 are also applicable. Monoacylation of unprotected phenylene diamine is described in EP 0 974 576.

There are quite a few compounds of formula V described in the literature. For example, the 5-Allyloxy-1H-indole-2-carboxylic acid is described in Moody, C. J., J. Chem. Soc. Perkin Trans. 1 (1984) 1333–1337; Julia, M., and Lallemand, J.-Y., Bull. Soc. Chim. Fr. (1973) 2046–2057.

In other cases compounds of formula V can be prepared by alkylation, silylation or acylation of compounds of formula VII

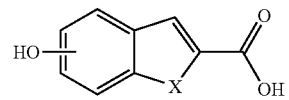

E.g. a benzoylation can be accomplished for example with benzoyl chloride in dichloromethane in the presence of pyridine.

There are quite a few compounds of formula VII described in the literature. For example, 5-Hydroxy-benzo [b]thiophene-2-carboxylic acid is described in Misra, T., et al., Spectrochim. Acta Part A 57 (2001) 2795–2808; 7-Hydroxy-benzofuran-2-carboxylic acid is described in Reichenstein, Helv. Chim. Acta 18 (1935) 816, 826.

The compounds according to the general formula I-A can be synthesized as exemplified in detail for 5-(2-Hydroxy-ethyl)-benzofuran-2-carboxylic acid (2-amino-phenyl)-amide ( Example 24), and by using the respective starting materials. Therefore the manufacture of the compounds according to the general formula I-A as well as the synthesis of the respective starting materials is within the ordinary skills of an organic chemist.

The compounds of formula I and I-A, as well as their pharmaceutically usable addition salts possess valuable pharmacological properties. It has been found that they possess antiproliferative and differentiation-inducing activity, which results in inhibition of tumor cell proliferation, induction of apoptosis and inhibition of invasion. Therefore these compounds are useful for the treatment of diseases such as cancer in humans or animals. Consequently a further embodiment of the present invention is the use of a compound of formula I or I-A for the treatment of cancer. Yet another embodiment is the use of a compound of formula I or I-A for the manufacture of corresponding medicaments for the inhibition of tumor growth.

The activity of the compounds according to this invention as HDAC inhibitors is demonstrated using a cellular acetylation assay. Therein acetylation of histones is monitored in PC3 cells. High acetylation correlates with inhibition of histone deacetylase by compounds. Cell viability is monitored in parallel to estimate the cytotoxicity of compounds.

PC3 cells, a human prostate carcinoma cell line, are seeded as 1800 cells per well of a 384-well microtiterplate in RPMI 1640 (including 5% FCS, 2 mM glutamine and pen/strep).

After 48 h at 37° C. pre-diluted compounds are added to a final concentration of 1 uM. Compounds are pre-diluted in dimethyl sulfoxide (DMSO) resulting in a final concentration of DMSO of 0.5% per well.

After 24 h incubation cell viability is determined by adding cell proliferation reagent WST-1 (Roche Molecular Biochemicals). Another 60 min later the optical density (OD) is measured (450 nm versus 690 nm).

After measurement the cell layer is prepared for the ELISA reaction. Medium is aspirated and cells are fixed in ethanol at −20° C. for 60 min. After washing with PBS/Tween the blocking solution (PBS/5% FCS/Tween) is added and the cell layer is washed again. Antibodies against acetylated histone H3 or H4 (rabbit polyklonal IgG, Upstate Biotechnologie) are added at a dilution of 1:200 for 60 min at 37° C. As a second antibody goat anti rabbit IgG (H+L) humanIgG adsorbed-HRP conjugate (Dako) is used (1:2000 diluted). Cells are washed 3 times and the peroxidase substrate ABTS is allowed to react for 30–60 min at 37° C. The OD is measured at 405 nm.

The percentage of acetylation is calculated after substraction of blank O.D.s:

$$\frac{\text{mean O.D. acetylation}}{\text{mean O.D. DMSO control}} \times 100\%$$
$$\frac{\text{mean O.D. WSTI}}{\text{mean O.D. DMSO control}}$$

| Ex.-No. | Compound Name | cell acetylation (PC3, 1 μM) [% of control] |
|---|---|---|
| | 4-acetylamino-N-(2-amino-phenyl)-benzamide (Reference Compound from EP0242851, Example 1) | 152 |
| 2 | 5-(3-Dimethylamino-propoxy)-benzo[b]thiophene-2-carboxylic acid (2-amino-phenyl)-amide | 209 |
| 3 | 5-(2-Diisopropylamino-ethoxy)-benzo[b]thiophene-2-carboxylic acid (2-amino-phenyl)-amide | 172 |
| 16 | 5-(2-Hydroxy-ethoxy)-benzo[b]thiophene-2-carboxylic acid (2-amino-phenyl)-amide | 156 |
| 24 | 5-(2-Hydroxy-ethyl)-benzofuran-2-carboxylic acid (2-amino-phenyl)-amide | 157 |

The effect of the compounds according to the present invention may further be assessed by the following test:

Male NMRI nu/nu-mice(n=15 per group), aged 8–10 weeks, are subcutaneously injected with 5*106 PC-3 prostate carcinoma cells. On day 10, animals with tumor volumes of about 150 mm$^3$ are randomly assigned to treatment groups. The test compound is administered as a microsuspension in 7.5% gelatine –0.22% NaCl—Suspension with an application volume of 10 ml/kg based on actual body weights. Once daily oral treatment is performed from approximately day 10 to day 27 on a 5–7 times per week treatment schedule.

The volume of the tumor is determined from the following equation: Volume of a tumor=1/2ab$^2$, where "a" and "b" are the long and the short diameters of the tumor, respectively. At the conclusion of treatment, measurement of the volume of the tumor is taken and compared to the original tumor volume to determine tumor volume reduction.

Yet another embodiment of the invention is a pharmaceutical composition containing as an active ingredient a compound of formula I or I-A as described herein before, if desired together with pharmaceutically acceptable adjuvants. Said medicaments, e.g. in the form of pharmaceutical preparations, can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical preparations can be obtained by processing the compounds according to this invention with pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Preferred pharmaceutical preparations comprise the following:

a) Tablet Formulation (Wet Granulation):

| Item | Ingredients | mg/tablet | | | |
|---|---|---|---|---|---|
| 1. | Compound of formula I or I-A | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

b) Capsule Formulation:

| Item | Ingredients | mg/capsule | | | |
|---|---|---|---|---|---|
| 1. | Compound of formula I or I-A | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

c) Formulation as a Micro-Suspension:

Weigh 4.0 g glass beads in custom made tube GL 25, 4 cm (the beads fill half of the tube).
Add 50 mg compound of formula I or I-A, disperse with spatulum and vortex.
Add 2 ml gelatin solution (weight beads: gelatin solution=2:1) and vortex.
Cap and wrap in aluminium foil for light protection.
Prepare a counter balance for the mill.
Mill for 4 hours, 20/s in a Retsch mill (for some substances up to 24 hours at 30/s).

Extract suspension from beads with two layers of filter (100 μm) on a filter holder, coupled to a recipient vial by centrifugation at 400 g for 2 min.
Move extract to measuring cylinder.
Repeat washing with small volumes(here 1 ml steps) until final volume is reached or extract is clear.
Fill up to final volume with gelatin and homogenise.

The dosage depends on various actors such as manner of administration, species, age and/or individual state of health. The doses to be administered daily are about 5–400 mg/kg, preferably about 10–100 mg/kg, and can be taken singly or distributed over several administrations.

The invention will now be illustrated in the following examples in which, unless otherwise stated:

i) evaporations were carried out by rotary evaporation in vacuo and work-up procedures were carried out after removal of residual solids such as drying agents by filtration;
(ii) operations were carried out at ambient temperature, that is in the range 18–25° C. and under an atmosphere of an inert gas such as argon or nitrogen;
(iii) column chromatography (by the flash procedure) and high pressure liquid chromatography (HPLC) were performed on Merck Kieselgel silica or Merck Lichroprep RP-18 reversed-phase silica obtained from E. Merck, Darmstadt, Germany;
(iv) yields are given for illustration only and are not necessarily the maximum attainable;
(v) melting points were determined using a Mettler SP62 automatic melting point apparatus, an oil-bath apparatus or a Kofler hot plate apparatus;
(vi) the structures of the products of the formula I were confirmed by nuclear (generally proton) magnetic resonance (NMR) and mass spectral techniques (Micromass Platform II machine using APCI or Micromass Platform ZMD using electrospray);
(vii) intermediates were not generally fully characterized and purity was assessed by thin layer chromatography;
(viii) the following abbreviations have been used:

| | |
|---|---|
| DMF | N,N-dimethylformamide; |
| DMSO | dimethylsulphoxide; |
| THF | tetrahydrofuran; |
| MeOH | methanol; |
| HCl | hydrochloric acid; |
| NaH | sodium hydride |
| $CH_2Cl_2$ | dichloromethane; |
| $H_2SO_4$ | sulphuric acid |
| sat. | saturated |
| sol. | solution |
| h | hour |
| d | days |
| rt | room temperature |
| eq | equivalent |
| mp | melting point [° C.] |
| MW calc'd | molecular weight, calculated [g/mol] |
| MW found | molecular weight, determined by mass spectrometry [g/mol] |

EXAMPLE 1

5-(2-Dimethylamino-ethoxy)-benzo[b]thiophene-2-carboxylic acid (2-amino-phenyl)-amide (1)

Step 1: O-Benzoyl-5-hydroxybenzothiophene-2-carboxylic acid (2)

To a suspension of 1168 mg (6.01 mmol) 5-Hydroxy-benzo[b]thiophene-2-carboxylic acid (Misra, T., et al., Spectrochim. Acta Part A 57 (2001) 2795–2808) in 30 ml dichloromethane were added 1186 mg (15 mmol) pyridine. The mixture was cooled to 0° C. and a solution of 1968 mg (14 mmol) benzoyl chloride in 15 ml dichloromethane was added within 0.5 h. The reaction mixture was warmed to room temperature and added to 5% aqueous citric acid. The aqueous phase was extracted twice with dichloromethane, the solvent of the organic phases was removed and the residue was chromatographed on silica gel (dichloromethane/methanol 19:1 and then dichloromethane/methanol 19:1 with 2% acetic acid) to yield 1180 mg (3.96 mmol) O-Benzoyl-5-hydroxybenzothiophene-2-carboxylic acid (2) as colorless crystals, mp. 235–236° C.

Step 2: Benzoic acid 2-(2-tert-butoxycarbonylamino-phenylcarbamoyl)-benzo[b]thiophen-5-yl ester (3)

To a suspension of 598 mg (2 mmol) O-Benzoyl-5-hydroxybenzothiophene-2-carboxylic acid (2) in 25 ml toluene at 80° C. DMF was added dropwise until the mixture became clear. 420 mg (3.5 mmol) thionyl chloride were added. After 4 h at this temperature the solvent of the reaction mixture was removed. The residue was dissolved in 20 ml dichloromethane and 1.0 ml pyridine and a solution of 396 mg mono-boc-orthophenylenediamine in 10 ml dichloromethane were added. After 12 h the reaction solution was poured on 5% aqueous citric acid. Extraction with dichloromethane, washing of the organic phase with aqueous citric acid and brine. The organic phase was dried over sodium sulfate, the solvent was evaporated and the residue subjected to silica gel chromatography (petrolether/ethylacetate 3:1). Benzoic acid 2-(2-tert-butoxycarbonylamino-phenylcarbamoyl)-benzo[b]thiophen-5-yl ester (3) was recrystallized from ethyl acetate to yield 790 mg (1.62 mmol) as colorless crystals, mp. 205–208° C. (decomp.).

Step 3: {2-[(5-Hydroxy-benzo[b]thiophene-2-carbonyl)-amino]-phenyl}-carbamic acid tert-butyl ester (4)

To a suspension of 732 mg (1.5 mmol) benzoic acid 2-(2-tert-butoxycarbonylamino-phenylcarbamoyl)-benzo[b]thiophen-5-yl ester (3) in 30 ml methanol was added 1.0 ml of a 5.4M solution of NaOMe in methanol. After 3 h at room temperature the reaction solution was poured on 5% aqueous citric acid. Extraction with ethyl acetate, washing of the organic phase with brine. The organic phase was dried over sodium sulfate, the solvent was evaporated and the residue subjected to silica gel chromatography (petrolether/ethyl acetate 3:1). {2-[(5-Hydroxy-benzo[b]thiophene-2-carbonyl)-amino]-phenyl}-carbamic acid tert-butyl ester (4) was recrystallized from ethyl acetate/diethyl ether to yield 546 mg (1.42 mmol) as colorless crystals, mp. 185° C. (decomp.).

Step 4: (2-{[5-(2-Dimethylamino-ethoxy)-benzo[b]thiophene-2-carbonyl]-amino}-phenyl)-carbamic acid tert-butyl ester (5)

To a solution of 77 mg (0.20 mmol) {2-[(5-Hydroxy-benzo[b]thiophene-2-carbonyl)-amino]-phenyl}-carbamic acid tert-butyl ester (4) in 3 ml ethyl acetate was added 120 mg potassium carbonate and 36 mg (0.25 mmol) (2-chloro-ethyl)-dimethyl-amine hydrochloride. The reaction mixture was heated at reflux for 16 h and poured into brine. The aqueous phase was extracted with ethyl acetate and the organic phase was dried over sodium sulfate, the solvent was evaporated and the residue subjected to silica gel chromatography (dichloromethane/methanol 19:1 and then 9:1). (2-{[5-(2-Dimethylamino-ethoxy)-benzo[b]thiophene-2-carbonyl]-amino}-phenyl)-carbamic acid tert-butyl ester (5) (72 mg, 0.158 mmol) was obtained as a colorless solid.

Step 5: 5-(2-Dimethylamino-ethoxy)-benzo[b]thiophene-2-carboxylic acid (2-amino-phenyl)-amide (1)

A solution of 72 mg (0.158 mmol) (2-{[5-(2-Dimethylamino-ethoxy)-benzo[b]thiophene-2-carbonyl]-amino}-phenyl)-carbamic acid tert-butyl ester (5) in 1.0 ml trifluoroacetic acid was stirred for 60 min at room temperature and then added to an aqueous solution of sodium bicarbonate. After extraction with ethyl acetate and removal of the solvent the residue was recrystallized from ethyl acetate/diethyl ether to yield 35 mg (0.10 mmol) 5-(2-Dimethylamino-ethoxy)-benzo[b]thiophene-2-carboxylic acid (2-amino-phenyl)-amide (1) as a yellow solid, mp. 191–193° C.

EXAMPLE 2

5-(3-Dimethylamino-propoxy)-benzo[b]thiophene-2-carboxylic acid (2-amino-phenyl)-amide (6)

Step 1: (2-{[5-(3-Dimethylamino-propoxy)-benzo[b]thiophene-2-carbonyl]-amino}-phenyl)-carbamic acid tert-butyl ester (7)

(7) was prepared from {2-[(5-Hydroxy-benzo[b]thiophene-2-carbonyl)-amino]-phenyl}-carbamic acid tert-butyl ester (4) in an analogous manner to that described for the preparation of (5) example 1, step 4.

Step 2: 5-(3-Dimethylamino-propoxy)-benzo[b]thiophene-2-carboxylic acid (2-amino-phenyl)-amide (6)

(6) was prepared from (2-{[5-(3-Dimethylamino-propoxy)-benzo[b]thiophene-2-carbonyl]-amino}-phenyl)-carbamic acid tert-butyl ester (7) in an analogous manner to that described for the preparation of (1) example 1, step 5; white solid, mp. 164–167° C.

EXAMPLE 3

5-(2-Diisopropylamino-ethoxy)-benzo[b]thiophene-2-carboxylic acid (2-amino-phenyl)-amide (8)

Step 1: (2-{[5-(2-Diisopropylamino-ethoxy)-benzo[b]thiophene-2-carbonyl]-amino}-phenyl)-carbamic acid tert-butyl ester (9)

(9) was prepared from {2-[(5-Hydroxy-benzo[b]thiophene-2-carbonyl)-amino]-phenyl}-carbamic acid tert-butyl ester (4) in an analogous manner to that described for the preparation of (5) example 1, step 4.

Step 2: 5-(2-Diisopropylamino-ethoxy)-benzo[b]thiophene-2-carboxylic acid (2-amino-phenyl)-amide (8)

(8) was prepared from (2-{[5-(2-Morpholin-4-yl-ethoxy)-benzo[b]thiophene-2-carbonyl]-amino}-phenyl)-carbamic acid tert-butyl ester (9) in an analogous manner to that described for the preparation of (1), example 1, step 5; yellow solid.

EXAMPLE 4

5-(2-Morpholin-4-yl-ethoxy)-benzo[b]thiophene-2-carboxylic acid (2-amino-phenyl)-amide (10)

Step 1: (2-{[5-(2-Morpholin-4-yl-ethoxy)-benzo[b]thiophene-2-carbonyl]-amino}-phenyl)-carbamic acid tert-butyl ester (11)

(11) was prepared from {2-[(5-Hydroxy-benzo[b]thiophene-2-carbonyl)-amino]-phenyl}-carbamic acid tert-butyl ester (4) in an analogous manner to that described for the preparation of (5) example 1, step 4.

Step 2: 5-(2-Morpholin-4-yl-ethoxy)-benzo[b]thiophene-2-carboxylic acid (2-amino-phenyl)-amide (10)

(10) was prepared from (2-{[5-(2-Morpholin-4-yl-ethoxy)-benzo[b]thiophene-2-carbonyl]-amino}-phenyl)-carbamic acid tert-butyl ester (11) in an analogous manner to that described for the preparation of (1) example 1, step 5; white solid, mp. 166–169° C.

EXAMPLE 5

7-(2-Dimethylamino-ethoxy)-benzofuran-2-carboxylic acid (2-amino-phenyl)-amide (12)

Step 1: 7-Benzoyloxy-benzofuran-2-carboxylic acid (13)

(13) was prepared from 7-Hydroxy-benzofuran-2-carboxylic acid (Reichenstein, Helv.Chim.Acta, 1935, 18, 816, 826.) in an analogous manner to that described for the preparation of (2) example 1, step 1, mp. 251–253° C. (subl.).

Step 2: Benzoic acid 2-(2-tert-butoxycarbonylamino-phenylcarbamoyl)-benzofuran-7-yl ester (14)

(14) was prepared from 7-Benzoyloxy-benzofuran-2-carboxylic acid (13) in an analogous manner to that described for the preparation of (3) example 1, step 2, mp. 206° C. (subl.).

Step 3: {2-[(7-Hydroxy-benzofuran-2-carbonyl)-amino]-phenyl}-carbamic acid tert-butyl ester (15)

(15) was prepared from benzoic acid 2-(2-tert-butoxycarbonylamino-phenylcarbamoyl)-benzofuran-7-yl ester (14) in an analogous manner to that described for the preparation of (3) example 1, step 3, mp. 168° C. (decomp.).

Step 4: (2-{[7-(2-Dimethylamino-ethoxy)-benzofuran-2-carbonyl]-amino}-phenyl)-carbamic acid tert-butyl ester (16)

(16) was prepared from {2-[(7-Hydroxy-benzofuran-2-carbonyl)-amino]-phenyl}-carbamic acid tert-butyl ester (15) in an analogous manner to that described for the preparation of (5) example 1, step 4.

Step 5: 7-(2-Dimethylamino-ethoxy)-benzofuran-2-carboxylic acid (2-amino-phenyl)-amide (12)

(12) was prepared from (2-{[7-(2-Dimethylamino-ethoxy)-benzofuran-2-carbonyl]-amino}-phenyl)-carbamic acid tert-butyl ester (16) in an analogous manner to that described for the preparation of (1) example 1, step 5; white solid, mp. 108–118° C.

EXAMPLE 6

7-(3-Dimethylamino-propoxy)-benzofuran-2-carboxylic acid (2-amino-phenyl)-amide (17)

Step 1: (2-{[7-(3-Dimethylamino-propoxy)-benzofuran-2-carbonyl]-amino}-phenyl)-carbamic acid tert-butyl ester (18)

(18) was prepared from {2-[(7-Hydroxy-benzofuran-2-carbonyl)-amino]-phenyl}-carbamic acid tert-butyl ester (15) in an analogous manner to that described for the preparation of (5) example 1, step 4.

Step 2: 7-(3-Dimethylamino-propoxy)-benzofuran-2-carboxylic acid (2-amino-phenyl)-amide (17)

(17) was prepared from (2-{[7-(3-Dimethylamino-propoxy)-benzofuran-2-carbonyl]-amino}-phenyl)-carbamic acid tert-butyl ester (18) in an analogous manner to that described for the preparation of (1) example 1, step 5; exact MW [M+H] calc'd: 354.18; MW found [M+H]: 354.2.

EXAMPLE 7

7-(2-Diisopropylamino-ethoxy)-benzofuran-2-carboxylic acid (2-amino-phenyl)-amide (19)

Step 1: (2-{[7-(2-Diisopropylamino-ethoxy)-benzofuran-2-carbonyl]-amino}-phenyl)-carbamic acid tert-butyl ester (20)

(20) was prepared from {2-[(7-Hydroxy-benzofuran-2-carbonyl)-amino]-phenyl}-carbamic acid tert-butyl ester (15) in an analogous manner to that described for the preparation of (5) example 1, step 4.

Step 2: 7-(2-Diisopropylamino-ethoxy)-benzofuran-2-carboxylic acid (2-amino-phenyl)-amide (19)

(19) was prepared from (2-{[7-(2-Diisopropylamino-ethoxy)-benzofuran-2-carbonyl]-amino}-phenyl)-carbamic acid tert-butyl ester (20) in an analogous manner to that described for the preparation of (1) example 1, step 5; exact MW [M+H] calc'd: 396.23; MW found [M+H]: 396.2.

EXAMPLE 8

7-(2-Piperidin-1-yl-ethoxy)-benzofuran-2-carboxylic acid (2-amino-phenyl)-amide (21)

Step 1: (2-{[7-(2-Piperidin-1-yl-ethoxy)-benzofuran-2-carbonyl]-amino}-phenyl)-carbamic acid tert-butyl ester (22)

(22) was prepared from {2-[(7-Hydroxy-benzofuran-2-carbonyl)-amino]-phenyl}-carbamic acid tert-butyl ester (15) in an analogous manner to that described for the preparation of (5) example 1, step 4.

Step 2: 7-(2-Piperidin-1-yl-ethoxy)-benzofuran-2-carboxylic acid (2-amino-phenyl)-amide (21)

(21) was prepared from (2-{[7-(2-Piperidin-1-yl-ethoxy)-benzofuran-2-carbonyl]-amino}-phenyl)-carbamic acid tert-butyl ester (22) in an analogous manner to that described for the preparation of (1) example 1, step 5; white solid; exact MW [M+H] calc'd: 380.20; MW found [M+H]: 380.2.

EXAMPLE 9

7-(2-Pyrrolidin-1-yl-ethoxy)-benzofuran-2-carboxylic acid (2-amino-phenyl)-amide (23)

Step 1: (2-{[7-(2-Pyrrolidin-1-yl-ethoxy)-benzofuran-2-carbonyl]-amino}-phenyl)-carbamic acid tert-butyl ester (24)

(24) was prepared from {2-[(7-Hydroxy-benzofuran-2-carbonyl)-amino]-phenyl}-carbamic acid tert-butyl ester (15) in an analogous manner to that described for the preparation of (5) example 1, step 4.

Step 2: 7-(2-Pyrrolidin-1-yl-ethoxy)-benzofuran-2-carboxylic acid (2-amino-phenyl)-amide (23)

(23) was prepared from (2-{[7-(2-Pyrrolidin-1-yl-ethoxy)-benzofuran-2-carbonyl]-amino}-phenyl)-carbamic acid tert-butyl ester (24) in an analogous manner to that described for the preparation of (1) example 1, step 5; yellow solid; exact MW [M+H] calc'd: 366.18; MW found [M+H]: 366.2.

EXAMPLE 10

7-(2-Morpholin-4-yl-ethoxy)-benzofuran-2-carboxylic acid (2-amino-phenyl)-amide (25)

Step 1: (2-{[7-(2-Morpholin-4-yl-ethoxy)-benzofuran-2-carbonyl]-amino}-phenyl)-carbamic acid tert-butyl ester (26)

(26) was prepared from {2-[(7-Hydroxy-benzofuran-2-carbonyl)-amino]-phenyl}-carbamic acid tert-butyl ester (15) in an analogous manner to that described for the preparation of (5) example 1, step 4.

Step 2: 7-(2-Morpholin-4-yl-ethoxy)-benzofuran-2-carboxylic acid (2-amino-phenyl)-amide (25)

(25) was prepared from [2-({5-[2-(tert-Butyl-dimethyl-silanyloxy)-ethoxy]-benzo[b]thiophene-2-carbonyl}-amino)-phenyl]-carbamic acid tert-butyl ester (26) in an analogous manner to that described for the preparation of (1) example 1, step 5; yellow solid; exact MW [M+H] calc'd: 382.18; MW found [M+H]: 382.0.

EXAMPLE 11

5-[2-(2-Methoxy-ethoxy)-ethoxy]-benzo[b]thiophene-2-carboxylic acid (2-amino-phenyl)-amide (27)

Step 1: [2-({5-[2-(2-Methoxy-ethoxy)-ethoxy]-benzo[b]thiophene-2-carbonyl}-amino)-phenyl]-carbamic acid tert-butyl ester (28)

To a solution of 77 mg (0.20 mmol) {2-[(5-Hydroxy-benzo[b]thiophene-2-carbonyl)-amino]-phenyl}-carbamic acid tert-butyl ester (4) in 3 ml acetonitrile was added 200 mg potassium carbonate and 0.3 ml 1-bromo-2-(2-methoxy-ethoxy)-ethane. The reaction mixture was heated at 100° C. for 90 min and poured into brine. The aqueous phase was extracted with ethyl acetate and the organic phase was dried over sodium sulfate, the solvent was evaporated and the residue subjected to silica gel chromatography (petrolether/ethyl acetate 2:1 and then 1:1). The product (28) (80 mg, 0.164 mmol) was obtained as a colorless oil.

Step 2: 5-[2-(2-Methoxy-ethoxy)-ethoxy]-benzo[b]thiophene-2-carboxylic acid (2-amino-phenyl)-amide (27)

A solution of 80 mg (0.164 mmol) of [2-({5-[2-(2-Methoxy-ethoxy)-ethoxy]-benzo[b]thiophene-2-carbonyl}-amino)-phenyl]-carbamic acid tert-butyl ester (28) in 1.0 ml trifluoroacetic acid was stirred for 45 min at room temperature and then added to an aqueous solution of sodium bicarbonate. After extraction with ethyl acetate and removal of the solvent the residue was recrystallized from ethyl acetate/heptane to yield 40 mg (0.103 mmol) of the desired product (27) as white crystals, mp. 167–168° C.

EXAMPLE 12

5-(2-Methoxy-ethoxy)-benzo[b]thiophene-2-carboxylic acid (2-amino-phenyl)-amide (29)

Step 1: (2-{[5-(2-Methoxy-ethoxy)-benzo[b]thiophene-2-carbonyl]-amino}-phenyl)-carbamic acid tert-butyl ester (30)

(30) was prepared from {2-[(5-Hydroxy-benzo[b]thiophene-2-carbonyl)-amino]-phenyl}-carbamic acid tert-butyl ester (4) in an analogous manner to that described for the preparation of (28) example 11, step 1.

Step 2: 5-(2-Methoxy-ethoxy)-benzo[b]thiophene-2-carboxylic acid (2-amino-phenyl)-amide (29)

(29) was prepared from (2-{[5-(2-Methoxy-ethoxy)-benzo[b]thiophene-2-carbonyl]-amino}-phenyl)-carbamic acid tert-butyl ester (30) in an analogous manner to that described for the preparation of (27) example 11, step 2; yellow solid, mp. 162–165° C.

EXAMPLE 13

7-[2-(2-Methoxy-ethoxy)-ethoxy]-benzofuran-2-carboxylic acid (2-amino-phenyl)-amide (31)

Step 1: [2-({7-[2-(2-Methoxy-ethoxy)-ethoxy]-benzofuran-2-carbonyl}-amino)-phenyl]-carbamic acid tert-butyl ester (32)

(32) was prepared from {2-[(7-Hydroxy-benzofuran-2-carbonyl)-amino]-phenyl}-carbamic acid tert-butyl ester (15) in an analogous manner to that described for the preparation of (28) example 11, step 1.

Step 2: 7-(2-Methoxy-ethoxy)-benzo[b]thiophene-2-carboxylic acid (2-amino-phenyl)-amide (29)

(31) was prepared from [2-({7-[2-(2-Methoxy-ethoxy)-ethoxy]-benzofuran-2-carbonyl}-amino)-phenyl]-carbamic acid tert-butyl ester (32) in an analogous manner to that described for the preparation of (27) example 11, step 2; exact MW [M+H] calc'd: 371.16; MW found [M+H]: 371.2.

EXAMPLE 14

7-(2-Methoxy-ethoxy)-benzofuran-2-carboxylic acid (2-amino-phenyl)-amide (33)

Step 1: (2-{[7-(2-Methoxy-ethoxy)-benzofuran-2-carbonyl]-amino}-phenyl)-carbamic acid tert-butyl ester (34)

(34) was prepared from {2-[(7-Hydroxy-benzofuran-2-carbonyl)-amino]-phenyl}-carbamic acid tert-butyl ester (15) in an analogous manner to that described for the preparation of (28) example 11, step 1.

Step 2: 7-(2-Methoxy-ethoxy)-benzofuran-2-carboxylic acid (2-amino-phenyl)-amide (33)

(33) was prepared from (2-{[7-(2-Methoxy-ethoxy)-benzofuran-2-carbonyl]-amino}-phenyl)-carbamic acid tert-butyl ester (34) in an analogous manner to that described for the preparation of (27) example 11, step 2; exact MW [M+H] calc'd: 327.13; MW found [M+H]: 327.0.

EXAMPLE 15

5-(2-Methoxy-ethoxy)-1H-indole-2-carboxylic acid (2-amino-phenyl)-amide (35)

Step 1: {2-[(5-Allyloxy-1H-indole-2-carbonyl)-amino]-phenyl}-carbamic acid tert-butyl ester (36)

(36) was prepared from 5-Allyloxy-1H-indole-2-carboxylic acid (Moody, C. J., J. Chem. Soc. Perkin Trans. 1 (1984) 1333–1337; Julia, M., and Lallemand, J.-Y., Bull. Soc. Chim. Fr. (1973) 2046–2057) in an analogous manner to that described for the preparation of (3) example 1, step 2; mp. 171–172° C.

Step 2: {2-[(5-Hydroxy-1H-indole-2-carbonyl)-amino]-phenyl}-carbamic acid tert-butyl ester (37)

To a solution of 3370 mg (8.27 mmol) {2-[(5-Allyloxy-1H-indole-2-carbonyl)-amino]-phenyl}-carbamic acid tert-butyl ester (36) in 100 ml methanol was added 5 ml water, 750 mg Pd (10% on C) and 300 mg p-toluenesulfonic acid. After heating at reflux for 6 h the reaction mixture was added to a 1:1 mixture of brine and saturated NaHCO$_3$ solution. The aqueous phase was extracted twice with ethyl acetate and the combined organic phases were washed with brine, dried over Na$_2$SO$_4$ and filtrated over celite. The solvent was removed and the residue was subjected to silica gel chromatography (petrolether/ethyl acetate 2:1). {2-[(5-Hydroxy-1H-indole-2-carbonyl)-amino]-phenyl}-carbamic acid tert-butyl ester (37) was recrystallized from diethyl ether/petrol ether to yield 1265 mg (3.44 mmol) crystalls, mp. 197° C. (decomposition).

Step 3: (2-{[5-(2-Methoxy-ethoxy)-1H-indole-2-carbonyl]-amino}-phenyl)-carbamic acid tert-butyl ester (38)

(38) was prepared {2-[(5-Hydroxy-1H-indole-2-carbonyl)-amino]-phenyl}-carbamic acid tert-butyl ester (37) in an analogous manner to that described for the preparation of (28), example 11, step 1.

Step 4: 5-(2-Methoxy-ethoxy)-1H-indole-2-carboxylic acid (2-amino-phenyl)-amide (35)

(35) was prepared: (2-{[5-(2-Methoxy-ethoxy)-1H-indole-2-carbonyl]-amino}-phenyl)-carbamic acid tert-butyl ester (38) in an analogous manner to that described for the preparation of (27) example 11, step 2; exact MW [M+H] calc'd: 326.15; MW found [M+H]: 326.3.

EXAMPLE 16

5-(2-Hydroxy-ethoxy)-benzo[b]thiophene-2-carboxylic acid (2-amino-phenyl)-amide (39)

Step 1: [2-({5-[2-(tert-Butyl-dimethyl-silanyloxy)-ethoxy]-benzo[b]thiophene-2-carbonyl}-amino)-phenyl]-carbamic acid tert-butyl ester (40)

To a solution of 96 mg (0.25 mmol) {2-[(5-Hydroxy-benzo[b]thiophene-2-carbonyl)-amino]-phenyl}-carbamic acid tert-butyl ester (4) in 5 ml acetonitrile was added 120 mg potassium carbonate and 0.3 ml (2-bromoethoxy)-tert-butyldimethylsilane. The reaction mixture was heated at reflux for 90 min and at 85° C. for 2 h and poured into 5% aqueous citric acid. The aqueous phase was extracted with ethyl acetate and the organic phase was dried over sodium sulfate, the solvent was evaporated and the residue subjected to silica gel chromatography (petrolether/ethylacetate 4:1 and then 9:1). [2-({5-[2-(tert-Butyl-dimethyl-silanyloxy)-ethoxy]-benzo[b]thiophene-2-carbonyl}-amino)-phenyl]-carbamic acid tert-butyl ester (40) (63 mg, 0.116 mmol) was obtained as a colorless solid.

Step 2: 5-(2-Hydroxy-ethoxy)-benzo[b]thiophene-2-carboxylic acid (2-amino-phenyl)-amide (39)

To a solution of 55 mg (0.100 mmol) [2-({5-[2-(tert-butyl-dimethyl-silanyloxy)-ethoxy]-benzo[b]thiophene-2-carbonyl}-amino)-phenyl]-carbamic acid tert-butyl ester (40) in 5 ml tetrahydrofurane was added 38 mg (0.120 mmol) tetra-n-butylammonium fluoride. The reaction mixture was stirred at room temperature for 1 h and poured into brine. The aqueous phase was extracted with ethyl acetate and the combined organic phases were washed brine and dried over sodium sulfate. The solvent was evaporated and the residue of (2-{[5-(2-Hydroxy-ethoxy)-benzo[b]thiophene-2-carbonyl]-amino}-phenyl)-carbamic acid tert-butyl ester was dissolved in 1.0 ml trifluoroacetic acid. The reaction mixture was stirred for 45 min at room temperature and then added to an aqueous solution of sodium bicarbonate. After extraction with ethyl acetate and removal of the solvent the residue was recrystallized from ethyl acetate/diethyl ether to yield 17 mg (0.052 mmol) of 5-(2-Hydroxy-ethoxy)-benzo[b]thiophene-2-carboxylic acid (2-amino-phenyl)-amide (39) as a white solid, mp. 215–216° C.

EXAMPLE 17

7-(2-Hydroxy-ethoxy)-benzofuran-2-carboxylic acid (2-amino-phenyl)-amide (41)

Step 1: [2-({7-[2-(tert-Butyl-dimethyl-silanyloxy)-ethoxy]-benzofuran-2-carbonyl}-amino)-phenyl]-carbamic acid tert-butyl ester (42)

(42) was prepared from {2-[(7-Hydroxy-benzofuran-2-carbonyl)-amino]-phenyl}-carbamic acid tert-butyl ester (15) in an analogous manner to that described for the preparation of (40) example 16, step 1; exact MW [M+H] calc'd: 327.13; MW found [M+H]: 327.0.

Step 2: 7-(2-Hydroxy-ethoxy)-benzofuran-2-carboxylic acid (2-amino-phenyl)-amide (41)

(41) was prepared from [2-({7-[2-(tert-Butyl-dimethyl-silanyloxy)-ethoxy]-benzofuran-2-carbonyl}-amino)-phenyl]-carbamic acid tert-butyl ester (38) in an analogous manner to that described for the preparation of (39) example 16, step 2; mp. 182–183° C.

EXAMPLE 18

5-(2-Hydroxy-ethoxy)-1H-indole-2-carboxylic acid (2-amino-phenyl)-amide (43)

Step 1: [2-({5-[2-(tert-Butyl-dimethyl-silanyloxy)-ethoxy]-1H-indole-2-carbonyl}-amino)-phenyl]-carbamic acid tert-butyl ester (44)

(44) was prepared from {2-[(5-Hydroxy-1H-indole-2-carbonyl)-amino]-phenyl}-carbamic acid tert-butyl ester (37) in an analogous manner to that described for the preparation of (40) example 16, step 1.

Step 2: 5-(2-Hydroxy-ethoxy)-1H-indole-2-carboxylic acid (2-amino-phenyl)-amide (43)

(43) was prepared [2-({5-[2-(tert-Butyl-dimethyl-silanyloxy)-ethoxy]-1H-indole-2-carbonyl}-amino)-phenyl]-carbamic acid tert-butyl ester (44) in an analogous manner to that described for the preparation of (39), example 16, step 2; mp. 222–223° C.

EXAMPLE 19

[2-(2-Amino-phenylcarbamoyl)-benzo[b]thiophen-5-yloxy]-acetic acid (45)

Step 1: [2-(2-tert-Butoxycarbonylamino-phenylcarbamoyl)-benzo[b]thiophen-5-yloxy]-acetic acid tert-butyl ester (46)

To a solution of 96 mg (0.25 mmol) {2-[(5-Hydroxy-benzo[b]thiophene-2-carbonyl)-amino]-phenyl}-carbamic acid tert-butyl ester (4) in 3 ml ethyl acetate was added 140 mg potassium carbonate and 60 mg (0.40 mmol) tert-butyl chloroacetate. The reaction mixture was heated at reflux for 16 h and poured into a saturated aqueous solution of ammonium chloride. The aqueous phase was extracted with ethyl acetate and the organic phase was dried over sodium sulfate, the solvent was evaporated and the residue subjected to silica gel chromatography (petrolether/ethyl acetate 4:1). The product fraction was recrystallized from heptane/diethylether to yield 57 mg (0.114 mmol) [2-(2-tert-Butoxycarbonylamino-phenylcarbamoyl)-benzo[b]thiophen-5-yloxy]-acetic acid tert-butyl ester (46), mp. 166° C.

Step 2: [2-(2-Amino-phenylcarbamoyl)-benzo[b]thiophen-5-yloxy]-acetic acid (45)

A solution of 48 mg (0.096 mmol) [2-(2-tert-Butoxycarbonylamino-phenylcarbamoyl)-benzo[b]thiophen-5-yloxy]-acetic acid tert-butyl ester (46) in 1.0 ml trifluoroacetic acid was stirred at room temperature for 2 h. 1 ml 1.7M aqueous NaOH was added dropwise and and the precipitated colorless crystals were filtered off and washed twice with water and four times with diethyl ether. 38 mg (0.96 mmol) [2-(2-Amino-phenylcarbamoyl)-benzo[b]thiophen-5-yloxy]-acetic acid (45), mp. 250° C. (decomposition).

EXAMPLE 20

[2-(2-Amino-phenylcarbamoyl)-benzofuran-7-yloxy]-acetic acid (47)

Step 1: [2-(2-tert-Butoxycarbonylamino-phenylcarbamoyl)-benzofuran-7-yloxy]-acetic acid tert-butyl ester (48)

(48) was prepared from {2-[(7-Hydroxy-benzofuran-2-carbonyl)-amino]-phenyl}-carbamic acid tert-butyl ester (15) in an analogous manner to that described for the preparation of (46) example 19, step 1, mp. 144–145° C.

Step 2: [2-(2-Amino-phenylcarbamoyl)-benzofuran-7-yloxy]-acetic acid (47)

(47) was prepared from [2-(2-tert-Butoxycarbonylamino-phenylcarbamoyl)-benzofuran-7-yloxy]-acetic acid tert-butyl ester (48) in an analogous manner to that described for the preparation of (45) example 19, step 2; mp.: 208–210° C.

EXAMPLE 21

[2-(2-Amino-phenylcarbamoyl)-1H-indol-5-yloxy]-acetic acid (49)

Step 1 [2-(2-tert-Butoxycarbonylamino-phenylcarbamoyl)-1H-indol-5-yloxy]-acetic acid tert-butyl ester (50)

(50) was prepared from {2-[(5-Hydroxy-1H-indole-2-carbonyl)-amino]-phenyl}-carbamic acid tert-butyl ester (37) in an analogous manner to that described for the preparation of (46) example 19, step 1, mp. 193° C. (decomposition).

Step 2: [2-(2-Amino-phenylcarbamoyl)-1H-indol-5-yloxy]-acetic acid (49)

(49) was prepared from [2-(2-tert-Butoxycarbonylamino-phenylcarbamoyl)-1H-indol-5-yloxy]-acetic acid tert-butyl ester (50) in an analogous manner to that described for the preparation of (45) example 19, step 2; mp.: >250° C. (decomposition).

EXAMPLE 22

5-(Pyridin-2-ylmethoxy)-benzo[b]thiophene-2-carboxylic acid (2-amino-phenyl)-amide (51)

Step 1: (2-{[5-(Pyridin-2-ylmethoxy)-benzo[b]thiophene-2-carbonyl]-amino}-phenyl)-carbamic acid tert-butyl ester (52)

To a solution of 77 mg (0.20 mmol) {2-[(5-Hydroxy-benzo[b]thiophene-2-carbonyl)-amino]-phenyl}-carbamic acid tert-butyl ester (4) in 3 ml ethyl acetate was added 200 mg potassium carbonate and 56 mg (0.22 mmol) 2-(bromomethyl)pyridine, hydrobromide. The reaction mixture was heated at reflux for 10 h and poured into brine. The aqueous phase was extracted with ethyl acetate and the organic phase was dried over sodium sulfate, the solvent was evaporated and the residue subjected to silica gel chromatography (petrolether/ethyl acetate 3:2) to yield (2-{[5-(Pyridin-2-ylmethoxy)-benzo[b]thiophene-2-carbonyl]-amino}-phenyl)-carbamic acid tert-butyl ester (52) (80 mg, 0.168 mmol) as colorless crystals.

Step 2: 5-(Pyridin-2-ylmethoxy)-benzo[b]thiophene-2-carboxylic acid (2-amino-phenyl)-amide (51)

A solution of 72 mg (0.151 mmol) of (2-{[5-(Pyridin-2-ylmethoxy)-benzo[b]thiophene-2-carbonyl]-amino}-phenyl)-carbamic acid tert-butyl ester (52) in 1.0 ml trifluoroacetic acid was stirred for 45 min at room temperature and then added to an aqueous solution of sodium bicarbonate. After extraction with ethyl acetate and removal of the solvent the residue was recrystallized from ethyl acetate to yield 33 mg (0.88 mmol) 5-(Pyridin-2-ylmethoxy)-benzo[b]thiophene-2-carboxylic acid (2-amino-phenyl)-amide (51) as white solid, mp. 205–207° C.

EXAMPLE 23

7-(Pyridin-2-ylmethoxy)-benzofuran-2-carboxylic acid (2-amino-phenyl)-amide (53)

Step 1: (2-{[7-(Pyridin-2-ylmethoxy)-benzofuran-2-carbonyl]-amino}-phenyl)-carbamic acid tert-butyl ester (54)

(54) was prepared from {2-[(7-Hydroxy-benzofuran-2-carbonyl)-amino]-phenyl}-carbamic acid tert-butyl ester (15) in an analogous manner to that described for the preparation of (52) example 22, step 1, exact MW [M+H] calc'd: 460.19; MW found [M+H]: 460.0.

Step 2:7-(Pyridin-2-ylmethoxy)-benzofuran-2-carboxylic acid (2-amino-phenyl)-amide (53)

(53) was prepared from (2-{[7-(Pyridin-2-ylmethoxy)-benzofuran-2-carbonyl]-amino}-phenyl)-carbamic acid tert-butyl ester (54) in an analogous manner to that described for the preparation of (51) example 22, step 2; mp.: 105–135° C.

EXAMPLE 24

5-(2-Hydroxy-ethyl)-benzofuran-2-carboxylic acid (2-amino-phenyl)-amide (55)

Step 1: {2-[(5-Bromo-benzofuran-2-carbonyl)-amino]-phenyl}-carbamic acid tert-butyl ester (56)

A mixture of 5290 mg (21.95 mmol) 5-Bromo-benzofuran-2-carboxylic acid (Owen, C. P., et al., J. Pharm. Pharmacol. 51 (1999) 427–434) and 20 ml thionyl chloride was heated at reflux for 4 h. The excess thionyl chloride was evaporated, 20 ml toluene were added and evaporated again. The residue was dissolved in 50 ml dichloromethane and 2.0 ml pyridine and a solution of 4373 mg (21.0 mmol) mono-boc-orthophenylenediamine in 30 ml dichloromethane were added at 0° C. After 12 h the precipitate was filtered off and washed with diethyl ether to give a first crop of 6550 mg (15.2 mmol) {2-[(5-Bromo-benzofuran-2-carbonyl)-amino]-phenyl}-carbamic acid tert-butyl ester (56). The solvent of the mother liquid was removed and 250 ml ethyl acetate were added to the residue. The organic phase was washed with 5% aqueous citric acid, saturated aqueous sodium bicarbonate solution and brine and dried over $Na_2SO_4$. 50 ml heptane were added to the solution and the solvent was evaporated to give another 1000 mg of (2.32 mmol) of {2-[(5-Bromo-benzofuran-2-carbonyl)-amino]-phenyl}-carbamic acid tert-butyl ester (56).

Step 2: {2-[(5-Vinyl-benzofuran-2-carbonyl)-amino]-phenyl}-carbamic acid tert-butyl ester (57)

To a mixture of 2027 mg (4.7 mmol) {2-[(5-Bromo-benzofuran-2-carbonyl)-amino]-phenyl}-carbamic acid tert-butyl ester (56) and 289 mg (0.25 mmol) $Pd(Ph_3)_4$ in 40 ml toluene were added 1.84 ml of a 5.4M solution of sodium methoxide in methanol and 957 mg (5.2 mmol) vinylboronic acid dibutyl ester and the solution was heated at 90° C. for 3 h. The reaction mixture was poured on 5% aqueous citric acid. Extraction with ethyl acetate, washing of the organic phase with brine. The organic phase was dried over sodium sulfate, the solvent was evaporated and the residue subjected to silica gel chromatography (petrolether/ethylacetate 2:1) to give 1530 mg (4.04 mmol) {2-[(5-Vinyl-benzofuran-2-carbonyl)-amino]-phenyl}-carbamic acid tert-butyl ester (57).

Step 3: (2-{[5-(2-Hydroxy-ethyl)-benzofuran-2-carbonyl]-amino}-phenyl)-carbamic acid tert-butyl ester (58)

A solution of 114 mg (o.30 mmol) {2-[(5-Vinyl-benzofuran-2-carbonyl)-amino]-phenyl}-carbamic acid tert-butyl ester (57), 5 ml THF and 1.4 ml of a 0.5M solution of 9-BBN in THF was stirred at rt for 4 h. A solution of 86 mg NaOH in 0.6 ml water was added and stirring was continued for further 2 h. The reaction mixture was washed with brine and the organic phase dried over sodium sulfate, the solvent was evaporated and the residue subjected to silica gel chromatography (petrolether/ethylacetate 1:1) to give 54 mg (0.136 mmol) (2-{[5-(2-Hydroxy-ethyl)-benzofuran-2-carbonyl]-amino}-phenyl)-carbamic acid tert-butyl ester (58).

Step 4: 5-(2-Hydroxy-ethyl)-benzofuran-2-carboxylic acid (2-amino-phenyl)-amide (55)

To a solution of 75 mg (0.189 mmol) (2-{[5-(2-Hydroxy-ethyl)-benzofuran-2-carbonyl]-amino}-phenyl)-carbamic acid tert-butyl ester (58) in 3 ml THF were added 1892 µl of 4M solution of HCl in dioxane. The reaction was stirred at 55° C. for 2 h. The solvent was evaporated, ethylacetate was added and the organic phase was washed with saturated aqueous sodium bicarbonate solution and brine and dried over $Na_2SO_4$. The solvent was removed to give 45 mg (0.152 mmol) 5-(2-Hydroxy-ethyl)-benzofuran-2-carboxylic acid (2-amino-phenyl)-amide (55); exact MW calc'd [M+H]: 297.12; MW found [M+H]: 297.1.

What is claimed is:
1. Compounds of formula I:

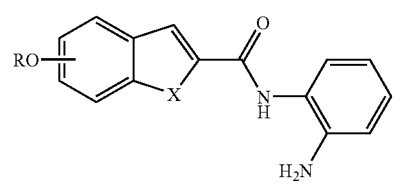

wherein:
(a) X represents N, S or O;
(b) R represents $CH_3-(O-CH_2CH_2)_n-$ or $C_1-C_6$-alkyl, which alkyl group is monosubstituted with $-CO_2H$, $-OH$, $R^1R^2N-$, pyridin-2-yl, pyrrolidin-1-yl, piperidino or morpholino;
(c) $R^1$ and $R^2$ are each independently a $C_1-C_6$ alkyl; and
(d) n is 1, 2, 3 or 4;
or pharmaceutically acceptable salts thereof.
2. The compounds according to claim 1, wherein:
(a) X represents N, S or O;
(b) R represents $R^1R^2N-C_1-C_6$-alkyl; and
(c) $R^1$ and $R^2$ are each independently a $C_1-C_6$ alkyl group.

3. A compound according to claim 1, wherein the compound is selected from the group consisting of:
- 5-(2-Dimethylamino-ethoxy)-benzo[b]thiophene-2-carboxylic acid (2-amino-phenyl)-amide,
- 5-(3-Dimethylamino-propoxy)-benzofuran-2-carboxylic acid (2-amino-phenyl)-amide,
- 5-(3-Dimethylamino-propoxy)-benzo[b]thiophene-2-carboxylic acid (2-amino-phenyl)-amide,
- 7-(2-Dimethylamino-ethoxy)-benzofuran-2-carboxylic acid (2-amino-phenyl)-amide, and
- 7-(2-Diisopropylamino-ethoxy)-benzofuran-2-carboxylic acid (2-amino-phenyl)-amide.

4. A compound according to claim 1, wherein the compound is selected from the group consisting of:
- 7-(3-Dimethylamino-propoxy)-benzofuran-2-carboxylic acid (2-amino-phenyl)-amide, and
- 5-(2-Diisopropylamino-ethoxy)-benzo[b]thiophene-2-carboxylic acid (2-amino-phenyl)-amide.

5. The compounds according to claim 1, wherein:
(a) X represents N, S or O;
(b) R represents a group $CH_3—(O—CH_2CH_2)_n—$; and
(c) n is 1, 2, 3 or 4.

6. A compound according to claim 1, wherein the compound is selected from the group consisting of:
- 5-(2-Methoxy-ethoxy)-1H-indole-2-carboxylic acid (2-amino-phenyl)-amide,
- 5-(2-Methoxy-ethoxy)-benzo[b]thiophene-2-carboxylic acid (2-amino-phenyl)-amide,
- 7-(2-Methoxy-ethoxy)-benzofuran-2-carboxylic acid (2-amino-phenyl)-amide,
- 7-[2-(2-Methoxy-ethoxy)-ethoxy]-benzofuran-2-carboxylic acid (2-amino-phenyl)-amide, and
- 5-[2-(2-Methoxy-ethoxy)-ethoxy]-benzo[b]thiophene-2-carboxylic acid (2-amino-phenyl)-amide.

7. The compounds according to claim 1, wherein:
(a) X represents N, S or O; and
(b) R represents a $C_1–C_6$-alkyl, monosubstituted with pyridin-2-yl, pyrrolidin-1-yl, piperidino or morpholino.

8. A compound according to claim 1, wherein the compound is selected from the group consisting of:
- 7-(Pyridin-2-ylmethoxy)-benzofuran-2-carboxylic acid (2-amino-phenyl)-amide,
- 5-(Pyridin-2-ylmethoxy)-benzo[b]thiophene-2-carboxylic acid (2-amino-phenyl)-amide,
- 7-(2-Pyrrolidin-1-yl-ethoxy)-benzofuran-2-carboxylic acid (2-amino-phenyl)-amide,
- 7-(2-Piperidin-1-yl-ethoxy)-benzofuran-2-carboxylic acid (2-amino-phenyl)-amide, and
- 5-(2-Morpholin-4-yl-ethoxy)-benzo[b]thiophene-2-carboxylic acid (2-amino-phenyl)-amide.

9. The compounds according to claim 1, wherein:
(a) X represents N, S or O; and
(b) R represents $C_1–C_6$-alkyl, monosubstituted with —$CO_2H$.

10. A compound according to claim 1, wherein the compound is selected from the group consisting of:
- 2-(2-Amino-phenylcarbamoyl)-benzofuran-7-yloxy]-acetic acid,
- 2-(2-Amino-phenylcarbamoyl)-benzo[b]thiophene-5-yloxy]-acetic acid, and
- 2-(2-Amino-phenylcarbamoyl)-1H-indole-5-yloxy]-acetic acid.

11. The compounds according to claim 1, wherein:
(a) X represents N, S or O; and
(b) R represents $C_1–C_6$-alkyl, monosubstituted with OH.

12. A compound according to claim 1, wherein the compound is selected from the group consisting of:
- 5-(2-Hydroxy-ethoxy)-benzo[b]thiophene-2-carboxylic acid (2-amino-phenyl)-amide,
- 5-(2-Hydroxy-ethoxy)-1H-indole-2-carboxylic acid (2-amino-phenyl)-amide, and
- 7-(2-Hydroxy-ethoxy)-benzofuran-2-carboxylic acid (2-amino-phenyl)-amide.

13. Compounds of formula I-A:

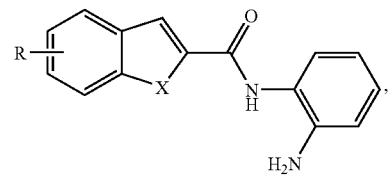

wherein X, R, $R^1$, $R^2$, and n are defined according to claim 1;
or pharmaceutically acceptable salts thereof.

14. The compounds according to claim 13, wherein:
(a) X represents O; and
(b) R is a $C_1–C_6$-alkyl, which alkyl group is monosubstituted with —OH.

15. A compound according to claim 13, wherein the compound is:
- 5-(2-Hydroxy-ethyl)-benzofuran-2-carboxylic acid (2-amino-phenyl)-amide.

16. A process for the manufacture of a compound of formula I of claim 1 comprising:
(a) reacting a compound of formula II:

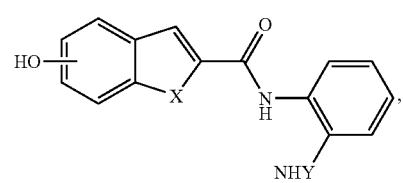

in which Y represents hydrogen or a suitable amino protecting group
with a compound of formula III:

R-LG    III, wherein reactive substituents, if present in R, are protected with a protecting group; and LG is a suitable leaving group; and
(b) subsequently, when Y represents a protected amino group, deprotection of this group as well as cleavage of protecting groups, if present, in R to obtain a compound of formula I of claim 1.

17. The process according to claim 16, further comprising the step of converting the compound of formula I prepared in step (b) to a pharmaceutically acceptable salt.

18. A pharmaceutical composition comprising:
a compound according to claim 1; and
a pharmaceutically acceptable carrier or excipient.

* * * * *